United States Patent
Nguyen et al.

(10) Patent No.: US 9,814,618 B2
(45) Date of Patent: Nov. 14, 2017

(54) DEVICES FOR DELIVERING ENERGY AND RELATED METHODS OF USE

(71) Applicant: Boston Scientific Scimed, Inc., Maple Grove, MN (US)

(72) Inventors: Man Minh Nguyen, Harvard, MA (US); Eric Karl Litscher, Hopkinton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 723 days.

(21) Appl. No.: 14/295,745

(22) Filed: Jun. 4, 2014

(65) Prior Publication Data

US 2014/0364926 A1    Dec. 11, 2014

Related U.S. Application Data

(60) Provisional application No. 61/831,997, filed on Jun. 6, 2013.

(51) Int. Cl.
*A61F 7/12* (2006.01)
*A61B 18/14* (2006.01)
(Continued)

(52) U.S. Cl.
CPC ............ *A61F 7/12* (2013.01); *A61B 18/1482* (2013.01); *A61B 18/1492* (2013.01);
(Continued)

(58) Field of Classification Search
CPC ......... A61B 18/00; A61B 18/08; A61B 18/14; A61B 18/1492; A61B 2018/00214;
(Continued)

(56) References Cited

U.S. PATENT DOCUMENTS

| 1,155,169 A | 9/1915 | Starkweather |
| 1,207,479 A | 12/1916 | Bisgaard |

(Continued)

FOREIGN PATENT DOCUMENTS

| AU | 2012/201427 A1 | 4/2012 |
| CN | 1078595 A | 11/1993 |

(Continued)

OTHER PUBLICATIONS

Abandoned U.S. Appl. No. 09/095,323, filed Jun. 10, 1998.
(Continued)

*Primary Examiner* — Matthew F Desanto
(74) *Attorney, Agent, or Firm* — Bookoff McAndrews, PLLC (57) ABSTRACT

A medical device is disclosed. The medical device may include an elongate member having a lumen extending at least partially between a proximal end and a distal end of the elongate member. The medical device may also include a plurality of legs coupled to a distal portion of the elongate member, and a distal end piece connected to each of the plurality of legs and located distally to the distal end of the elongate member. The medical device may also include an actuating member coupled to the distal end piece and extending between the plurality of legs and through the lumen. The reciprocal movement of the actuating member may be configured to reversibly move the plurality of legs from a first position to a second position. The medical device may also include a stopping member coupled to the actuating member and configured to limit a movement of the actuating member.

16 Claims, 3 Drawing Sheets

(51) Int. Cl.
*A61F 7/00* (2006.01)
*A61B 90/00* (2016.01)
*A61B 17/00* (2006.01)
*A61B 18/00* (2006.01)

(52) U.S. Cl.
CPC .............. *A61B 90/03* (2016.02); *A61F 7/007* (2013.01); *A61B 2017/00809* (2013.01); *A61B 2017/00867* (2013.01); *A61B 2018/0016* (2013.01); *A61B 2018/00196* (2013.01); *A61B 2018/00267* (2013.01); *A61B 2018/00434* (2013.01); *A61B 2018/00541* (2013.01); *A61B 2018/00577* (2013.01); *A61B 2018/1467* (2013.01); *A61B 2018/1475* (2013.01); *A61B 2090/034* (2016.02); *A61F 2007/0001* (2013.01); *A61F 2007/126* (2013.01)

(58) Field of Classification Search
CPC .. A61B 2018/00267; A61B 2018/1405; A61B 2018/1407; A61B 18/1482; A61B 2018/144; A61B 2018/1415
See application file for complete search history.

(56) References Cited

U.S. PATENT DOCUMENTS

| | | |
|---|---|---|
| 2,072,346 A | 3/1937 | Smith |
| 3,320,957 A | 5/1967 | Sokolik |
| 3,568,659 A | 3/1971 | Karnegis |
| 3,667,476 A | 6/1972 | Muller |
| 3,692,029 A | 9/1972 | Adair |
| 4,461,283 A | 7/1984 | Doi |
| 4,503,855 A | 3/1985 | Maslanka |
| 4,522,212 A | 6/1985 | Gelinas et al. |
| 4,565,200 A | 1/1986 | Cosman |
| 4,567,882 A | 2/1986 | Heller |
| 4,584,998 A | 4/1986 | McGrail |
| 4,612,934 A | 9/1986 | Borkan |
| 4,643,186 A | 2/1987 | Rosen et al. |
| 4,674,497 A | 6/1987 | Ogasawara |
| 4,706,688 A | 11/1987 | Don Michael et al. |
| 4,709,698 A | 12/1987 | Johnston et al. |
| 4,799,479 A | 1/1989 | Spears |
| 4,802,492 A | 2/1989 | Grunstein |
| 4,825,871 A | 5/1989 | Cansell |
| 4,827,935 A | 5/1989 | Geddes et al. |
| 4,862,886 A | 9/1989 | Clarke et al. |
| 4,920,978 A | 5/1990 | Colvin |
| 4,955,377 A | 9/1990 | Lennox et al. |
| 4,967,765 A | 11/1990 | Turner et al. |
| 4,976,709 A | 12/1990 | Sand |
| 5,010,892 A | 4/1991 | Colvin et al. |
| 5,019,075 A | 5/1991 | Spears et al. |
| 5,053,033 A | 10/1991 | Clarke |
| 5,056,519 A | 10/1991 | Vince |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,106,360 A | 4/1992 | Ishiwara et al. |
| 5,116,864 A | 5/1992 | March et al. |
| 5,117,828 A | 6/1992 | Metzger et al. |
| 5,135,517 A | 8/1992 | McCoy |
| 5,152,286 A | 10/1992 | Sitko et al. |
| 5,170,803 A | 12/1992 | Hewson et al. |
| 5,174,288 A | 12/1992 | Bardy et al. |
| 5,188,602 A | 2/1993 | Nichols |
| 5,191,883 A | 3/1993 | Lennox et al. |
| 5,215,103 A | 6/1993 | Desai |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,279,565 A | 1/1994 | Klein et al. |
| 5,281,218 A | 1/1994 | Imran |
| 5,292,331 A | 3/1994 | Boneau |
| 5,293,869 A | 3/1994 | Edwards et al. |
| 5,309,910 A | 5/1994 | Edwards et al. |
| 5,311,866 A | 5/1994 | Kagan et al. |
| 5,313,943 A | 5/1994 | Houser et al. |
| 5,322,503 A | 6/1994 | Desai |
| 5,324,284 A | 6/1994 | Imran |
| 5,343,936 A | 9/1994 | Beatenbough et al. |
| 5,345,936 A | 9/1994 | Pomeranz et al. |
| 5,366,443 A | 11/1994 | Eggers et al. |
| 5,368,591 A | 11/1994 | Lennox et al. |
| 5,370,644 A | 12/1994 | Langberg |
| 5,370,679 A | 12/1994 | Atlee, III |
| 5,374,287 A | 12/1994 | Rubin |
| 5,383,917 A | 1/1995 | Desai et al. |
| 5,389,098 A | 2/1995 | Tsuruta et al. |
| 5,394,880 A | 3/1995 | Atlee, III |
| 5,396,887 A | 3/1995 | Imran |
| 5,400,783 A | 3/1995 | Pomeranz et al. |
| 5,409,469 A | 4/1995 | Schaerf |
| 5,411,025 A | 5/1995 | Webster |
| 5,415,166 A | 5/1995 | Imran |
| 5,415,656 A | 5/1995 | Tihon et al. |
| 5,417,687 A | 5/1995 | Nardella et al. |
| 5,423,744 A | 6/1995 | Gencheff et al. |
| 5,423,811 A | 6/1995 | Imran et al. |
| 5,425,703 A | 6/1995 | Feiring |
| 5,431,696 A | 7/1995 | Atlee, III |
| 5,433,730 A | 7/1995 | Alt |
| 5,443,470 A | 8/1995 | Stern et al. |
| 5,454,782 A | 10/1995 | Perkins |
| 5,456,667 A | 10/1995 | Ham et al. |
| 5,456,684 A | 10/1995 | Schmidt et al. |
| 5,458,596 A | 10/1995 | Lax et al. |
| 5,464,404 A | 11/1995 | Abela et al. |
| 5,465,717 A | 11/1995 | Imran et al. |
| 5,471,982 A | 12/1995 | Edwards et al. |
| 5,474,530 A | 12/1995 | Passafaro et al. |
| 5,478,309 A | 12/1995 | Sweezer et al. |
| 5,496,271 A | 3/1996 | Burton et al. |
| 5,496,311 A | 3/1996 | Abele et al. |
| 5,500,011 A | 3/1996 | Desai |
| 5,505,728 A | 4/1996 | Ellman et al. |
| 5,505,730 A | 4/1996 | Edwards |
| 5,509,411 A | 4/1996 | Littmann et al. |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,558,073 A | 9/1996 | Pomeranz et al. |
| 5,562,608 A | 10/1996 | Sekins et al. |
| 5,562,619 A | 10/1996 | Mirarchi et al. |
| 5,571,088 A | 11/1996 | Lennox et al. |
| 5,578,067 A | 11/1996 | Ekwall et al. |
| 5,582,609 A | 12/1996 | Swanson et al. |
| 5,588,432 A | 12/1996 | Crowley |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,623,940 A | 4/1997 | Daikuzono |
| 5,624,439 A | 4/1997 | Edwards et al. |
| 5,626,618 A | 5/1997 | Ward et al. |

(56) References Cited

U.S. PATENT DOCUMENTS

| | | |
|---|---|---|
| 5,630,425 A | 5/1997 | Panescu et al. |
| 5,630,794 A | 5/1997 | Lax et al. |
| 5,634,471 A | 6/1997 | Fairfax et al. |
| 5,647,870 A | 7/1997 | Kordis et al. |
| 5,678,535 A | 10/1997 | DiMarco |
| 5,680,860 A | 10/1997 | Imran |
| 5,681,280 A | 10/1997 | Rusk et al. |
| 5,681,308 A | 10/1997 | Edwards et al. |
| 5,693,078 A | 12/1997 | Desai et al. |
| 5,699,799 A | 12/1997 | Xu et al. |
| 5,707,352 A | 1/1998 | Sekins et al. |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,728,094 A | 3/1998 | Edwards |
| 5,730,128 A | 3/1998 | Pomeranz et al. |
| 5,730,726 A | 3/1998 | Klingenstein |
| 5,730,741 A | 3/1998 | Horzewski et al. |
| 5,740,808 A | 4/1998 | Panescu et al. |
| 5,752,518 A | 5/1998 | McGee et al. |
| 5,755,753 A | 5/1998 | Knowlton |
| 5,759,158 A | 6/1998 | Swanson |
| 5,769,846 A | 6/1998 | Edwards et al. |
| 5,772,590 A | 6/1998 | Webster |
| 5,779,669 A | 7/1998 | Haissaguerre et al. |
| 5,779,698 A | 7/1998 | Clayman et al. |
| 5,782,239 A | 7/1998 | Webster |
| 5,782,795 A | 7/1998 | Bays |
| 5,782,827 A | 7/1998 | Gough et al. |
| 5,782,899 A | 7/1998 | Imran |
| 5,792,064 A | 8/1998 | Panescu et al. |
| 5,795,303 A | 8/1998 | Swanson et al. |
| 5,807,306 A | 9/1998 | Shapland et al. |
| 5,810,807 A | 9/1998 | Ganz et al. |
| 5,814,029 A | 9/1998 | Hassett |
| 5,823,189 A | 10/1998 | Kordis |
| 5,824,359 A | 10/1998 | Khan et al. |
| 5,827,277 A | 10/1998 | Edwards |
| 5,833,632 A | 11/1998 | Jacobsen et al. |
| 5,836,946 A | 11/1998 | Diaz et al. |
| 5,836,947 A | 11/1998 | Fleischman et al. |
| 5,837,001 A | 11/1998 | Mackey |
| 5,843,075 A | 12/1998 | Taylor |
| 5,843,077 A | 12/1998 | Edwards |
| 5,846,238 A | 12/1998 | Jackson et al. |
| 5,848,969 A | 12/1998 | Panescu et al. |
| 5,848,972 A | 12/1998 | Triedman et al. |
| 5,849,011 A | 12/1998 | Jones et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | LeVeen et al. |
| 5,871,443 A | 2/1999 | Edwards et al. |
| 5,871,523 A | 2/1999 | Fleischman et al. |
| 5,873,865 A | 2/1999 | Horzewski et al. |
| 5,876,340 A | 3/1999 | Tu et al. |
| 5,876,399 A | 3/1999 | Chia et al. |
| 5,881,727 A | 3/1999 | Edwards |
| 5,882,346 A | 3/1999 | Pomeranz et al. |
| 5,891,135 A | 4/1999 | Jackson et al. |
| 5,891,136 A | 4/1999 | McGee et al. |
| 5,891,138 A | 4/1999 | Tu et al. |
| 5,893,847 A | 4/1999 | Kordis |
| 5,897,554 A | 4/1999 | Chia et al. |
| 5,899,882 A | 5/1999 | Waksman et al. |
| 5,904,651 A | 5/1999 | Swanson et al. |
| 5,904,711 A | 5/1999 | Flom et al. |
| 5,906,636 A | 5/1999 | Casscells, III et al. |
| 5,908,445 A | 6/1999 | Whayne et al. |
| 5,908,446 A | 6/1999 | Imran |
| 5,911,218 A | 6/1999 | DiMarco |
| 5,916,235 A | 6/1999 | Guglielmi |
| 5,919,147 A | 7/1999 | Jain |
| 5,921,999 A | 7/1999 | Dileo |
| 5,928,228 A | 7/1999 | Kordis et al. |
| 5,935,079 A | 8/1999 | Swanson et al. |
| 5,941,869 A | 8/1999 | Patterson et al. |
| 5,951,494 A | 9/1999 | Wang et al. |
| 5,954,661 A | 9/1999 | Greenspon et al. |
| 5,954,662 A | 9/1999 | Swanson et al. |
| 5,954,717 A | 9/1999 | Behl et al. |
| 5,957,842 A | 9/1999 | Littmann et al. |
| 5,957,961 A | 9/1999 | Maguire et al. |
| 5,964,753 A | 10/1999 | Edwards |
| 5,964,756 A | 10/1999 | McGaffigan et al. |
| 5,964,796 A | 10/1999 | Imran |
| 5,968,087 A | 10/1999 | Hess et al. |
| 5,971,983 A | 10/1999 | Lesh |
| 5,972,026 A | 10/1999 | Laufer et al. |
| 5,979,456 A | 11/1999 | Magovern |
| 5,980,563 A | 11/1999 | Tu et al. |
| 5,991,650 A | 11/1999 | Swanson et al. |
| 5,992,419 A | 11/1999 | Sterzer et al. |
| 5,993,462 A | 11/1999 | Pomeranz et al. |
| 5,997,534 A | 12/1999 | Tu et al. |
| 5,999,855 A | 12/1999 | DiMarco |
| 6,003,517 A | 12/1999 | Sheffield et al. |
| 6,004,269 A | 12/1999 | Crowley et al. |
| 6,006,755 A | 12/1999 | Edwards |
| 6,009,877 A | 1/2000 | Edwards |
| 6,010,500 A | 1/2000 | Sherman et al. |
| 6,014,579 A | 1/2000 | Pomeranz et al. |
| 6,016,437 A | 1/2000 | Tu et al. |
| 6,023,638 A | 2/2000 | Swanson |
| 6,024,740 A | 2/2000 | Lesh et al. |
| 6,029,091 A | 2/2000 | De La Rama et al. |
| 6,032,673 A | 3/2000 | Savage et al. |
| 6,033,397 A | 3/2000 | Laufer et al. |
| 6,033,404 A | 3/2000 | Melzer et al. |
| 6,036,687 A | 3/2000 | Laufer et al. |
| 6,036,689 A | 3/2000 | Tu et al. |
| 6,039,731 A | 3/2000 | Taylor et al. |
| 6,045,549 A | 4/2000 | Smethers et al. |
| 6,045,550 A | 4/2000 | Simpson et al. |
| 6,050,992 A | 4/2000 | Nichols |
| 6,053,172 A | 4/2000 | Hovda et al. |
| 6,056,744 A | 5/2000 | Edwards |
| 6,056,769 A | 5/2000 | Epstein et al. |
| 6,066,132 A | 5/2000 | Chen et al. |
| 6,071,279 A | 6/2000 | Whayne et al. |
| 6,071,280 A | 6/2000 | Edwards et al. |
| 6,071,281 A | 6/2000 | Burnside et al. |
| 6,071,282 A | 6/2000 | Fleischman |
| 6,083,255 A | 7/2000 | Laufer et al. |
| 6,092,528 A | 7/2000 | Edwards |
| 6,102,886 A | 8/2000 | Lundquist et al. |
| 6,119,030 A | 9/2000 | Morency |
| 6,123,703 A | 9/2000 | Tu et al. |
| H0001905 H | 10/2000 | Hill |
| 6,129,751 A | 10/2000 | Lucchesi et al. |
| 6,139,527 A | 10/2000 | Laufer et al. |
| 6,142,993 A | 11/2000 | Whayne et al. |
| 6,143,013 A | 11/2000 | Samson et al. |
| 6,149,647 A | 11/2000 | Tu et al. |
| 6,152,899 A | 11/2000 | Farley et al. |
| 6,159,194 A | 12/2000 | Eggers et al. |
| 6,179,833 B1 | 1/2001 | Taylor |
| 6,183,468 B1 | 2/2001 | Swanson et al. |
| 6,198,970 B1 | 3/2001 | Freed et al. |
| 6,200,311 B1 | 3/2001 | Danek et al. |
| 6,200,332 B1 | 3/2001 | Del Giglio |
| 6,200,333 B1 | 3/2001 | Laufer |
| 6,210,367 B1 | 4/2001 | Carr |
| 6,214,002 B1 | 4/2001 | Fleischman et al. |
| 6,216,043 B1 | 4/2001 | Swanson et al. |
| 6,216,044 B1 | 4/2001 | Kordis |
| 6,217,576 B1 | 4/2001 | Tu et al. |
| 6,231,571 B1 | 5/2001 | Ellman et al. |
| 6,235,024 B1 | 5/2001 | Tu |
| 6,241,727 B1 | 6/2001 | Tu et al. |
| 6,251,104 B1 | 6/2001 | Kesten et al. |
| 6,254,598 B1 | 7/2001 | Edwards et al. |

(56) References Cited

U.S. PATENT DOCUMENTS

| | | |
|---|---|---|
| 6,258,083 B1 | 7/2001 | Daniel et al. |
| 6,258,087 B1 | 7/2001 | Edwards et al. |
| 6,270,476 B1 | 8/2001 | Santoianni et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,296,639 B1 | 10/2001 | Truckai et al. |
| 6,299,633 B1 | 10/2001 | Laufer |
| 6,322,559 B1 | 11/2001 | Daulton et al. |
| 6,322,584 B2 | 11/2001 | Ingle et al. |
| 6,325,795 B1 | 12/2001 | Lindemann et al. |
| 6,338,727 B1 | 1/2002 | Noda et al. |
| 6,338,836 B1 | 1/2002 | Kuth et al. |
| 6,355,031 B1 | 3/2002 | Edwards et al. |
| 6,379,349 B1 | 4/2002 | Muller et al. |
| 6,379,352 B1 | 4/2002 | Reynolds et al. |
| 6,409,723 B1 | 6/2002 | Edwards |
| 6,411,852 B1 | 6/2002 | Danek et al. |
| 6,416,511 B1 | 7/2002 | Lesh et al. |
| 6,423,058 B1 | 7/2002 | Edwards et al. |
| 6,423,105 B1 | 7/2002 | Iijima et al. |
| 6,425,895 B1 | 7/2002 | Swanson et al. |
| 6,428,538 B1 | 8/2002 | Blewett et al. |
| 6,438,400 B1 | 8/2002 | Beard et al. |
| 6,440,129 B1 | 8/2002 | Simpson |
| 6,442,435 B2 | 8/2002 | King et al. |
| 6,460,545 B2 | 10/2002 | Kordis |
| 6,488,673 B1 | 12/2002 | Laufer et al. |
| 6,493,589 B1 | 12/2002 | Medhkour et al. |
| 6,496,738 B2 | 12/2002 | Carr |
| 6,514,246 B1 | 2/2003 | Swanson et al. |
| 6,526,320 B2 | 2/2003 | Mitchell |
| 6,529,756 B1 | 3/2003 | Phan et al. |
| 6,544,226 B1 | 4/2003 | Gaiser et al. |
| 6,544,262 B2 | 4/2003 | Fleischman |
| 6,547,788 B1 | 4/2003 | Maguire et al. |
| 6,572,612 B2 | 6/2003 | Stewart et al. |
| 6,575,623 B2 | 6/2003 | Werneth |
| 6,582,427 B1 | 6/2003 | Goble et al. |
| 6,582,430 B2 | 6/2003 | Hall |
| 6,589,235 B2 | 7/2003 | Wong et al. |
| 6,610,054 B1 | 8/2003 | Edwards et al. |
| 6,613,002 B1 | 9/2003 | Clark et al. |
| 6,620,159 B2 | 9/2003 | Hegde |
| 6,626,903 B2 | 9/2003 | McGuckin et al. |
| 6,634,363 B1 | 10/2003 | Danek et al. |
| 6,638,273 B1 | 10/2003 | Farley et al. |
| 6,638,275 B1 | 10/2003 | McGaffigan et al. |
| 6,640,120 B1 | 10/2003 | Swanson et al. |
| 6,645,199 B1 | 11/2003 | Jenkins et al. |
| 6,645,200 B1 | 11/2003 | Koblish et al. |
| 6,652,548 B2 | 11/2003 | Evans et al. |
| 6,669,693 B2 | 12/2003 | Friedman |
| 6,673,068 B1 | 1/2004 | Berube |
| 6,673,290 B1 * | 1/2004 | Whayne .................. A61B 18/08 264/135 |
| 6,692,492 B2 | 2/2004 | Simpson et al. |
| 6,699,243 B2 | 3/2004 | West et al. |
| 6,714,822 B2 | 3/2004 | King et al. |
| 6,723,091 B2 | 4/2004 | Goble et al. |
| 6,743,197 B1 | 6/2004 | Edwards |
| 6,749,604 B1 | 6/2004 | Eggers et al. |
| 6,749,606 B2 | 6/2004 | Keast et al. |
| 6,749,607 B2 | 6/2004 | Edwards et al. |
| 6,767,347 B2 | 7/2004 | Sharkey et al. |
| 6,770,070 B1 | 8/2004 | Balbierz |
| 6,802,843 B2 | 10/2004 | Truckai et al. |
| 6,805,131 B2 | 10/2004 | Kordis |
| 6,827,717 B2 | 12/2004 | Brommersma et al. |
| 6,837,888 B2 | 1/2005 | Ciarrocca et al. |
| 6,840,243 B2 | 1/2005 | Deem et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,866,662 B2 | 3/2005 | Fuimaono et al. |
| 6,869,437 B1 | 3/2005 | Hausen et al. |
| 6,872,206 B2 | 3/2005 | Edwards et al. |
| 6,881,213 B2 | 4/2005 | Ryan et al. |
| 6,893,436 B2 | 5/2005 | Woodard et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,917,834 B2 | 7/2005 | Koblish et al. |
| 6,954,977 B2 | 10/2005 | Maguire et al. |
| 7,001,382 B2 | 2/2006 | Gallo, Sr. |
| 7,027,869 B2 | 4/2006 | Danek et al. |
| 7,043,307 B1 | 5/2006 | Zelickson et al. |
| 7,104,987 B2 | 9/2006 | Biggs et al. |
| 7,118,568 B2 | 10/2006 | Hassett et al. |
| 7,122,033 B2 | 10/2006 | Wood |
| 7,186,251 B2 | 3/2007 | Malecki et al. |
| 7,198,635 B2 | 4/2007 | Danek et al. |
| 7,200,445 B1 | 4/2007 | Dalbec et al. |
| 7,211,041 B2 | 5/2007 | Mueller |
| 7,425,212 B1 * | 9/2008 | Danek .................. A61B 18/00 606/42 |
| 7,507,232 B1 | 3/2009 | Garito et al. |
| 7,556,624 B2 | 7/2009 | Laufer et al. |
| 7,931,647 B2 | 4/2011 | Wizeman et al. |
| 2002/0072737 A1 | 6/2002 | Belden et al. |
| 2002/0147391 A1 | 10/2002 | Morency |
| 2002/0173785 A1 | 11/2002 | Spear et al. |
| 2003/0050631 A1 | 3/2003 | Mody et al. |
| 2003/0065371 A1 | 4/2003 | Satake |
| 2003/0109778 A1 | 6/2003 | Rashidi |
| 2003/0159700 A1 | 8/2003 | Laufer et al. |
| 2003/0233099 A1 | 12/2003 | Danaek et al. |
| 2004/0031494 A1 | 2/2004 | Danek et al. |
| 2004/0153056 A1 | 8/2004 | Muller et al. |
| 2004/0182399 A1 | 9/2004 | Danek et al. |
| 2004/0193243 A1 | 9/2004 | Mangiardi et al. |
| 2004/0249401 A1 | 12/2004 | Rabiner et al. |
| 2005/0010138 A1 | 1/2005 | Mangiardi et al. |
| 2005/0010270 A1 | 1/2005 | Laufer |
| 2005/0049586 A1 | 3/2005 | Daniel et al. |
| 2005/0096644 A1 | 5/2005 | Hall et al. |
| 2005/0154386 A1 | 7/2005 | West et al. |
| 2005/0182431 A1 | 8/2005 | Hausen et al. |
| 2005/0203503 A1 | 9/2005 | Edwards et al. |
| 2005/0240176 A1 | 10/2005 | Oral et al. |
| 2005/0272971 A1 | 12/2005 | Ohnishi et al. |
| 2005/0288664 A1 | 12/2005 | Ford et al. |
| 2006/0062808 A1 | 3/2006 | Laufer et al. |
| 2006/0089637 A1 | 4/2006 | Werneth et al. |
| 2006/0100652 A1 | 5/2006 | Beaupre |
| 2006/0135953 A1 | 6/2006 | Kania et al. |
| 2006/0212032 A1 | 9/2006 | Daniel et al. |
| 2006/0247617 A1 | 11/2006 | Danek et al. |
| 2006/0247618 A1 | 11/2006 | Kaplan et al. |
| 2006/0247619 A1 | 11/2006 | Kaplan et al. |
| 2006/0247746 A1 | 11/2006 | Danek et al. |
| 2006/0259028 A1 | 11/2006 | Utley et al. |
| 2006/0259029 A1 | 11/2006 | Utley et al. |
| 2006/0259030 A1 | 11/2006 | Utley et al. |
| 2006/0265035 A1 | 11/2006 | Yachi et al. |
| 2006/0282071 A1 | 12/2006 | Utley et al. |
| 2007/0021745 A1 | 1/2007 | McIntyre et al. |
| 2007/0055228 A1 | 3/2007 | Berg et al. |
| 2007/0093802 A1 | 4/2007 | Danek et al. |
| 2007/0100390 A1 | 5/2007 | Danaek et al. |
| 2007/0106108 A1 | 5/2007 | Hermann et al. |
| 2007/0106292 A1 | 5/2007 | Kaplan et al. |
| 2007/0106296 A1 | 5/2007 | Laufer et al. |
| 2007/0118184 A1 | 5/2007 | Danek et al. |
| 2007/0123958 A1 | 5/2007 | Laufer |
| 2007/0123961 A1 | 5/2007 | Danek et al. |
| 2007/0208336 A1 | 9/2007 | Kim et al. |
| 2008/0103498 A1 | 5/2008 | West et al. |
| 2008/0172048 A1 | 7/2008 | Martin et al. |
| 2008/0312649 A1 | 12/2008 | Guerra et al. |
| 2008/0312650 A1 | 12/2008 | Daniel et al. |
| 2008/0319436 A1 | 12/2008 | Daniel et al. |
| 2009/0018538 A1 | 1/2009 | Webster et al. |
| 2009/0043301 A1 | 2/2009 | Jarrard et al. |

(56) References Cited

U.S. PATENT DOCUMENTS

| | | |
|---|---|---|
| 2009/0043302 A1 | 2/2009 | Ford et al. |
| 2009/0069797 A1 | 3/2009 | Danek et al. |
| 2009/0171274 A1* | 7/2009 | Harlev ................ A61B 5/0422 |
| | | 604/95.04 |
| 2009/0275864 A1 | 11/2009 | Hirai |
| 2010/0042096 A1 | 2/2010 | Ellman |
| 2010/0094288 A1 | 4/2010 | Kerr |
| 2010/0160906 A1 | 6/2010 | Jarrard |
| 2010/0193569 A1 | 8/2010 | Yates et al. |
| 2010/0292684 A1 | 11/2010 | Cybulski et al. |
| 2011/0028963 A1 | 2/2011 | Gilbert |
| 2011/0071518 A1 | 3/2011 | Gilbert |
| 2011/0087213 A1 | 4/2011 | Messerly et al. |
| 2012/0330299 A1 | 12/2012 | Webster et al. |

FOREIGN PATENT DOCUMENTS

| | | |
|---|---|---|
| EP | 189329 A3 | 6/1987 |
| EP | 0873710 A2 | 10/1998 |
| EP | 908713 A1 | 4/1999 |
| EP | 908150 B1 | 5/2003 |
| EP | 1297795 B1 | 8/2005 |
| EP | 2 170 459 B1 | 2/2014 |
| EP | 2170459 B1 | 2/2014 |
| FR | 2659240 B1 | 7/1997 |
| JP | 7289557 A | 11/1995 |
| RU | 2053814 C1 | 2/1996 |
| RU | 2091054 C1 | 9/1997 |
| WO | WO-8911311 A1 | 11/1989 |
| WO | WO-9304734 A1 | 3/1993 |
| WO | WO-9502370 A3 | 3/1995 |
| WO | WO-9510322 A1 | 4/1995 |
| WO | WO-9604860 A1 | 2/1996 |
| WO | WO-9610961 A1 | 4/1996 |
| WO | WO-9732532 A1 | 9/1997 |
| WO | WO-9733715 A1 | 9/1997 |
| WO | WO-9737715 A1 | 10/1997 |
| WO | WO-9844854 A1 | 10/1998 |
| WO | WO-9846150 A1 | 10/1998 |
| WO | WO-9852480 A1 | 11/1998 |
| WO | WO-9856234 A1 | 12/1998 |
| WO | WO-9856324 A1 | 12/1998 |
| WO | WO-9903413 A1 | 1/1999 |
| WO | WO-9858681 A3 | 3/1999 |
| WO | WO-9913779 A2 | 3/1999 |
| WO | WO-9934741 A1 | 7/1999 |
| WO | WO-9944506 A1 | 9/1999 |
| WO | WO-9945855 A1 | 9/1999 |
| WO | WO-0051510 A1 | 9/2000 |
| WO | WO-0062699 A2 | 10/2000 |
| WO | WO-0103642 A1 | 1/2001 |
| WO | WO-0232334 A1 | 4/2002 |
| WO | WO-2006007284 A2 | 1/2006 |
| WO | WO-2006044581 A2 | 4/2006 |
| WO | WO-2008051706 A2 | 5/2008 |
| WO | WO-2014/043687 A2 | 3/2014 |

OTHER PUBLICATIONS

Abandoned U.S. Appl. No. 09/244,173, filed Feb. 4, 1999.
Abandoned U.S. Appl. No. 11/551,639, filed Oct. 20, 2006.
Expired U.S. Appl. No. 60/951,655, filed Jul. 24, 2007.
Dierkesmann R., "Indication and Results of Endobronchial Laser Therapy," Lung, 1990, 168, 1095-1102.
Hogg J. C., "The Pathology of Asthma," APMIS, 1997, 105 (10), 735-745.
International Search Report and Written Opinion dated Oct. 1, 2008, International Application No. PCT/US2008/065867 (8 pages).
Ivanyuta O.M., et al., "Effect of Low-Power Laser Irradiation of Bronchial Mucosa on the State of Systemic and Local Immunity in Patients with Chronic Bronchitis," Problemy Tuberkuleza, 1991, 6, 26-29.
Johnson S. R., et al., "Synthetic Functions of Airway Smooth Muscle in Asthma," Trends Pharmacol. Sci., 1997, 18 (8), 288-292.
Macklem P. T., "Mechanical Factors Determining Maximum Bronchoconstriction," European Respiratory Journal, 1989, 6, 516s-519s.
Netter F.H., "Respiratory System: A Compilation of Paintings Depicting Anatomy and Embryology, Physiology, Pathology, Pathophysiology, and Clinical Features and Treatment of Diseases,In The CIBA Collection of Medical Illustrations M.B. Divertie, ed., Summit: New Jerse," 1979, 7, 119-135.
Provotorov V.M., et al., "The Clinical Efficacy of Treating Patients with Nonspecific Lung Diseases Using Low-energy Laser Irradiation and Intrapulmonary Drug Administration," Terapevticheskii Arkhiv, 1991, 62 (12), 18-23.
Vorotnev A.I., et al., "The Treatment of Patients with Chronic Obstructive Bronchitis by Using a Low-power Laser at a General Rehabilitation Center," Terapevticheskii Arkhiv, 1997, 69 (3), 17-19.
Wiggs B.R., et al., "On the Mechanism of Mucosal Folding in Normal and Asthmatic Airways," Journal of Applied Physiology, 1997, 83 (6), 1814-1821.
Co-pending U.S. Appl. No. 12/640,644, filed Dec. 17, 2009, Inventor Jerry Jarrard.

* cited by examiner

DEVICES FOR DELIVERING ENERGY AND RELATED METHODS OF USE

CROSS-REFERENCE TO RELATED APPLICATION

This patent application claims the benefits of priority under 35 U.S.C. §119 to U.S. Provisional Patent Application No. 61/831,997, filed Jun. 6, 2013, the entirety of which is incorporated herein by reference.

FIELD OF THE DISCLOSURE

This disclosure relates generally to devices and methods for delivering thermal energy to a wall. More particularly, this disclosure relates to devices and methods treating a pulmonary system and airway. More particularly, the disclosure relates to medical and surgical devices and methods for treating a lung having at least one symptom of obstructive pulmonary disease. The disclosure also relates to devices and methods for delivering energy to an airway tissue of the lung in a controlled manner.

BACKGROUND OF THE DISCLOSURE

Devices that deliver energy to walls are often utilized to treat medical conditions. One such condition is, chronic obstructive pulmonary disease (COPD), which is a progressive disease that can cause obstruction in a lung airway limiting airflow into and out of the lung. Hence, a patient suffering from COPD may have difficulty breathing. There may be a number of factors responsible for COPD, such as smooth muscle contraction, excessive mucus production, thickening of the airway wall due to inflammation, and alteration of structures around the airway. More particularly, excessive and inappropriate constriction of airway smooth muscle (ASM) located within the walls of lung airways of such patients may be a contributory factor for COPD. Thus, reducing excessive ASM can provide a therapeutic benefit for treating COPD. Minimally invasive techniques have been developed to successfully reduce and/or eliminate excessive ASM.

An example of a minimally invasive technique for reducing (e.g., shrinking or debulking) excessive ASM involves delivery of thermal energy to the airway wall using a catheter. To apply the treatment, the catheter is positioned at a desired location within the airway. An electrode array at the tip of the catheter is expanded to contact the airway wall. The electrodes are expanded manually by squeezing a handle of the catheter to the desired expansion amount. In some embodiments, the treatment may involve damaging nerve tissue in airways of the pulmonary system to reduce the resting tone of smooth muscle tissue.

The use of conventional minimally invasive techniques may still be suboptimal. For example, it is possible to over-expand the electrodes by squeezing too much on the handle, leading to possible damage of the electrodes and adjacent body tissue. In addition, a user may not apply enough pressure to the handle, resulting in the electrodes not contacting or delivering thermal energy uniformly to the airway wall.

Thus, there are still shortcomings related to the known minimally invasive techniques utilized to reduce at least one symptom of COPD.

SUMMARY OF THE DISCLOSURE

The present disclosure is directed to a medical device for delivering thermal energy to wall of a tissue of a human body in a controlled manner for carrying out certain medical procedures, including general and surgical procedures.

In one aspect of the disclosure, a medical device may include an elongate member having a lumen extending at least partially between a proximal end and a distal end of the elongate member. The medical device may also include a plurality of legs coupled to a distal portion of the elongate member, and a distal end piece connected to each of the plurality of legs and located distally to the distal end of the elongate member. The medical device may also include an actuating member coupled to the distal end piece and extending between the plurality of legs and through the lumen. Reciprocal movement of the actuating member may be configured to reversibly move the plurality of legs from a first position to a second position. The medical device may also include a stopping member coupled to the actuating member and configured to limit a movement of the actuating member.

Various embodiments of the disclosure may also include one or more of the following aspects: wherein the stopping member may be configured to limit a movement of the actuating member along a longitudinal axis of the elongate member; wherein at least a portion of the stopping member may be disposed within the distal end piece; wherein the stopping member may define a lumen configured to receive a portion of the actuating member; wherein the actuating member may further include a protrusion disposed at a distal end of the actuating member, the protrusion may be configured to compress the stopping member; wherein the protrusion may be a disc attached to the distal end of the actuating member, wherein the disc may include a width greater than a width of the stopping member lumen; wherein the disc may engage a distal end of the stopping member to limit the movement of the actuating member; a support disposed around the actuating member and connected to the stopping member, the support may be configured to support a proximal end of the stopping member; wherein the stopping member may be formed in at least one end of each of the plurality of legs; wherein the stopping member may be disposed proximal to the plurality of legs; wherein the stopping member may be disposed between two portions of the actuating member; wherein the plurality of legs may be compressed in the first position, and are configured to bow outwardly from a longitudinal axis in the second position; and wherein the stopping member may be in a first configuration when the plurality of legs are in the first position, and in a second configuration when the plurality of legs are in the second position.

In another aspect, the present disclosure may be directed to a medical device having an elongate member having a lumen extending between a proximal end and a distal end of the elongate member. The medical device may also include a plurality of legs extending from the distal end of the elongate member. At least one of the legs may include an electrode for delivering energy, and each of the plurality of legs may include a distal end. The medical device may also include a distal end piece connected to the distal end of each of the plurality of legs, and an actuating member coupled to the distal end piece and extending between the plurality of legs and through the lumen. The actuating member may be configured to reversibly move the plurality of legs from a first position to a second position. The plurality of legs may move from the first position to the second position when a proximal force is applied to the actuating member, and the plurality of legs may move from the second position to the first position when the proximal force is released. The medical device may also include a stopping member coupled to the actuating member configured to limit a movement of the actuating member.

Various embodiments of the present disclosure may also include one or more of the following aspects: wherein at least a portion of the stopping member may be disposed within the distal end piece; and wherein the actuating member may further include a protrusion disposed at a distal end of the actuating member, the protrusion may be configured to engage the stopping member when the actuating member is moved in the proximal direction.

In yet another aspect, the present disclosure may be directed to a method of delivering energy to a wall of a body lumen using a medical device. The method may include inserting the medical device into the body lumen, and pulling proximally an actuating member to radially expand an expandable member at a distal end of the medical device. The method may also include limiting the radial expansion of the expandable member by compressing a stopping member coupled to the actuating member, and applying energy to the wall of the body lumen via the expandable member.

Various embodiments of the present disclosure may also include: wherein the radial expansion of the expandable member may be limited by limiting a movement of the actuating member along a longitudinal axis of the medical device; wherein at least a portion of the stopping member may be disposed within a distal end piece of the medical device; and wherein the stopping member may define a lumen configured to receive a portion of the actuating member.

Additional characteristics, features, and advantages of the disclosed subject matter will be set forth in part in the description that follows, and in part will be apparent from the description, or may be learned by practicing the disclosure. The characteristics and features of the disclosure can be realized and attained by way of the elements and combinations particularly pointed out in the appended claims.

It is to be understood that both the foregoing general description and the following detailed description are exemplary and explanatory only, and are not restrictive of the disclosed subject matter.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made to certain exemplary embodiments of the present disclosure, examples of which are illustrated in the accompanying drawings. Wherever possible, the same reference numbers will be used throughout the drawings to refer to the same or like parts. The term "distal" refers to the end farthest away from a medical professional when introducing a device in a patient. The term "proximal" refers to the end closest to the medical professional when placing a device in the patient.

Overview

Embodiments of the present disclosure relate to devices configured for delivering consistent thermal energy to wall of a tissue of a human body and methods thereof. For example, embodiments of the disclosed device(s) may facilitate delivery of thermal energy to a wall of an airway in a lung in a controlled manner to reduce, shrink, debulk, or otherwise eliminate excessive airway smooth muscle (ASM) to decrease at least one symptom of chronic or reversible obstructive pulmonary disease, including, but not limited to, asthma.

Exemplary Embodiments

The embodiments disclosed herein can be employed along with an elongate device, which may be an endoscopic system that functions as a means to introduce and deliver the disclosed embodiments to a target site within a patient's body. However, it should be noted that embodiments of the present disclosure may be used along with other introduction devices, sheaths, or systems, such as bronchoscopes, trocars, endoscopes, catheter sheaths, laparoscopes, colonoscopes, ureterscope, or the like.

Figure 1:
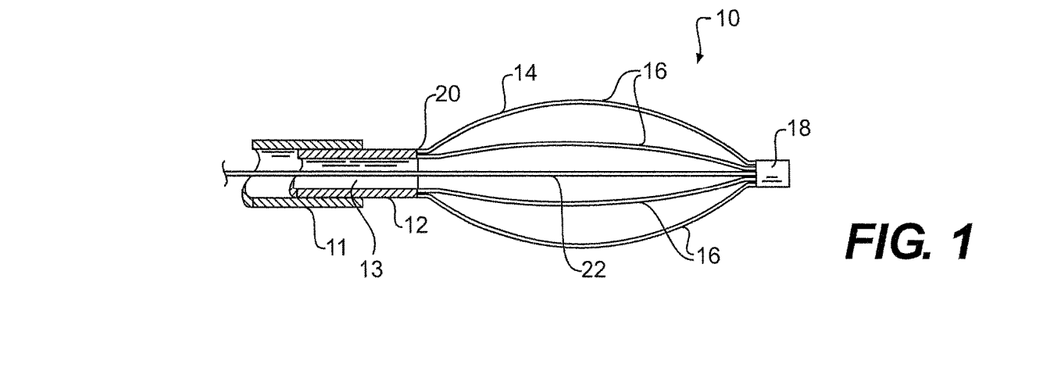
FIG. 1 is a schematic view of an exemplary medical device, according to one embodiment of the present disclosure.

FIG. 1 is a schematic view of an exemplary medical device for delivering thermal energy to a treatment site in accordance with the present disclosure. A medical device 10 may be configured to traverse through narrow lumens of the body having walls, e.g., airways of the lungs to reach the treatment site.

The medical device 10 may include a sheath 11 through which an elongate member 12 may pass. The elongate member 12 may have a distal end 20, a proximal end (not shown), and a lumen 13 extending between distal end 20 and the proximal end. Although the elongate member 12 may define a single lumen 13, the elongate member 12 may alternatively define a plurality of lumens. In some embodiments, the plurality of lumens may extend the entire length of the elongate member 12. In other embodiments, there may be additional lumens that only extend partly through elongate member 12. In some embodiments, the elongate member 12 may be coupled, or extended to other parts of the medical device 10.

Further, the elongate member 12 and the sheath 11 may have a tubular structure defining a circular cross-section. The respective cross-sectional profiles of elongate member 12 and sheath 11 may be relatively easy to assemble, remove, and/or use while being utilized in conjunction with any other elongated devices such as, e.g., a bronchoscope. Alternatively, elongate member 12 and the sheath 11 may have other configurations, such as, but not limited to, an elliptical cross-sectional profile, etc.

The sheath 11 may be a flexible, hollow member having dimensions that allow elongate member 12 to pass therethrough. That is, sheath 11 may have a diameter that is larger than the diameter of elongate member 12 and is smaller than the diameter of both a bronchoscope (or other suitable device) and a body lumen such as an airway. In particular, the dimensions of the sheath 11 may be compact enough to pass through the airway, while still allowing the elongate member 12 to be disposed therein.

Elongate member 12 and the sheath 11 may include any suitable flexible and/or biocompatible material, including, but not limited to, metals, polymers, alloys, and the like. In at least some embodiments, the elongate member 12 and the sheath 11 are made from one or more of nitinol, silicone, or the like. According to one embodiment, the material may exhibit sufficient flexibility to be maneuvered through the body lumens and positioned within without causing any injury to the surrounding tissue, such as, e.g., airways.

Elongate member 12 may further include a basket 14 having a plurality of legs 16 coupled to a distal portion (not shown) of the elongate member 12. In an alternative embodiment, basket 14 may be replaced with an inflatable, expandable member (e.g., a balloon). Each of the legs 16 may be configured to include an electrode disposed along the longitudinal length of the legs 16. Further, each electrode may be positioned along the legs 16 such that the electrode may be able to touch a tissue surface such as an airway wall to deliver energy to a treatment site when the legs 16 are expanded. However, each of the legs 16 may further include more than one electrode to transfer energy at the treatment site. The electrodes may be coupled to the legs 16 by any suitable means known in the art. In some embodiments, each of the legs 16 may include a conductive material, and the ends of legs 16 may be covered with an insulating material to leave an exposed active region.

Structurally, each of the legs 16 may have proximal portions emerging out of the lumen of the elongate member 12. In some embodiments, each of the legs 16 may have proximal portions joined or otherwise coupled to each other through an adhesive (or other attachment structure or material) and may form a proximal joint passing through the elongate member 12. Each of the legs 16 may have proximal portions extending continuously from the distal end 20 of the elongate member 12, as shown in FIG. 1. Further, distal portions of each of the legs 16 may be connected to each other by various mechanisms known in the art such as soldering, gluing, welding, using attachment structures, or the like.

Each of the legs 16 may be spaced at approximately any desired interval or equal intervals to form the basket 14. For instance, FIG. 1 may depict four legs 16 spaced at approximately 90 degree intervals around the basket 14. In an embodiment having five legs 16, e.g., the legs 16 may be spaced at approximately 72 degree intervals to form the basket 14. Therefore, the number and degree interval of the legs 16 around the basket 14 may depend upon various requirements such as size of the target airway, desired contact between each leg 16 and the airway wall, or the like.

Each of the legs 16 may have a length such that the basket 14 may be able to expand and contact a wall of the airway and traverse through the narrow airways of the lungs. Also, the legs 16 may include a sufficient thickness and modulus so as not to break or otherwise plastically deform while expanding and contracting during the procedure.

The basket 14 may be configured to reciprocate from a first, compressed position to a second, expanded position, e.g., a bowing outwardly state, and vice versa. The basket 14 may be configured to expand radially from the first position to the second position. In the second position, the basket 14 may be expanded such that arch shaped portions of the legs 16 contact a wall surface of an airway to deliver energy.

The legs forming the basket 14 may be formed from a resilient, highly tensile, and biocompatible material that may not deform (e.g., elastically) while expanding radially. Examples of such materials may include, but are not limited to silicone, super elastic alloy, stainless steel, shape memory alloy such as nitinol or the like. In some embodiments, the legs 16 may be made from the same material as that of the elongate member 12, and define a circular cross-sectional profile. However, the legs 16 may have other cross-sectional profiles such as elliptical, rectangular, or the like.

As discussed above, distal portions of each of the legs 16 may be joined together and further may be encompassed by a covering such as a distal cap or distal end piece 18. Thus, the distal cap 18 may be located distally to the distal end 20 of the elongate member 12. The distal cap 18 may have a diameter configured to facilitate insertion of the medical device 10 into narrow airways of the lungs without harming the airways. Accordingly, distal cap 18 may have an atraumatic configuration. Moreover, the distal cap 18 may be sized such that the distal cap 18 may be able to enter, pass through, and exit through a bronchoscope (or other suitable device) and the narrow airway.

The distal cap 18 may be a hollow cylindrical elongate member and configured to allow the distal portions of the legs 16 to pass through or into. In one embodiment, e.g., a distal end of distal cap 18 may be closed. The distal cap 18 may be long enough to substantially encompass a distal portion of the legs 16. Further details of the internal structure of the distal cap 18 will be discussed in conjunction with subsequent figures. In some embodiments, distal cap 18 may be electrically conductive with an insulating cover.

The distal cap 18 may have a circular cross-sectional profile. However, the distal cap 18 may have other cross-sections such as elliptical, rectangular, polygonal, non-symmetrical, or the like.

The distal cap 18 may be formed from a flexible, biocompatible material. Examples of such materials may include, but are not limited to, silicone, shape memory alloys such as nitinol, or the like.

Next, an actuating member 22 such as a pull wire may be configured to extend from a proximal portion (not shown) of the medical device 10, passing through the lumen of the elongate member 12, extending through the basket 14 and between the legs 16, coupling the distal portions of the legs 16 and the distal cap 18, and further extending to pass through the distal cap 18. The actuating member 22 may be configured to move back and forth (i.e., reciprocate) as a force is applied manually or autonomously on the actuating member 22 at the proximal portion of the medical device 10. In some embodiments, actuating member 22 may be a braided pull wire and/or include a plurality of pull wires.

The actuating member 22 may be configured as an elongated wire that extends from the proximal portion of the medical device 10, through the basket 14, toward the distal cap 18.

The actuating member 22 may be formed from any suitable biocompatible material. Alternatively, actuating member 22 may be a rod, string, knot or other suitable mechanism capable of reciprocal movement. Examples of suitable materials may include but are not limited to nitinol, other shape memory alloys, stainless steel, silicone, or the like.

A proximal portion of the medical device 10 may be configured to emerge out of a distal end of an elongate device such as a bronchoscope (not shown). The bronchoscope may be employed to view internal structure of bronchioles. At an extreme proximal end (not shown) of the medical device 10, there may be a handle (not shown) that may be configured to be manually or autonomously squeezed. At the handle or other actuator, there may be a plug (not shown) for connection to an electrosurgical generator that may be configured to provide electrical energy to the medical device 10.

Figure 2:
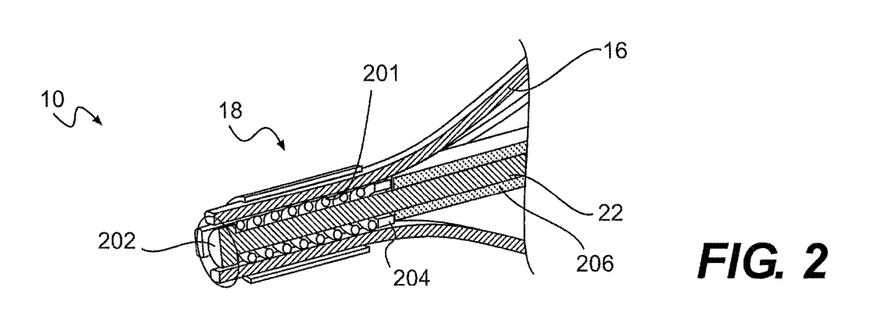
FIG. 2 is a cross-sectional side view of the medical device of FIG. 1 depicting a stopping member in an uncompressed position.

FIG. 2 is a cross-sectional view of the medical device 10 of FIG. 1 depicting the actuating member 22 in an unactivated position. As shown in FIG. 2, the distal cap 18 may encompass a portion of the distal portions of the legs 16 including the electrodes and the actuating member 22. Further, a stopping member 201 such as, e.g., a coiled spring, may be operatively coupled to and encompass the actuating member 22. The stopping member 201 may define a lumen that is configured to receive a distal portion of the actuating member 22. The stopping member 201 may be configured to limit a movement of the actuating member 22 in at least the proximal direction along a longitudinal axis of the elongate member 12. A substantial portion of the stopping member 201 may be disposed within the distal cap 18.

The stopping member 201 may compress and expand when a force is applied or released at the handle of the medical device 10. Stopping member 201 may include compression springs, coiled springs, Bellville washers, compressible polymeric materials, compressible elastic tubes, hydraulic or pneumatic bladders, inflatable members, leaf springs, rubber bands, sponges, or the like.

The stopping member 201 may be formed from a flexible, resilient, compressible, and/or biocompatible material. Example of such materials may include, but are not limited to, stainless steel, shape memory alloys, polymers, other suitable materials having elastic properties, or the like. In some embodiments, non-elastic materials can also be used to construct the stopping member 201, if desired.

Further, a protrusion 202 such as a disc may be disposed at a distalmost end of the actuating member 22. The protrusion 202 may be configured to engage a distal end of the stopping member 201 to limit the movement of the actuating member 22 in e.g., a proximal direction. The protrusion 202 may have a width greater than a width of the lumen of the stopping member 201. In some embodiments, protrusion 202 may be fixed to the distal ends of legs 16 such that when actuating member 22 is actuated (e.g., in a proximal direction), both protrusion 202 and the distal ends of legs 16 also move proximally.

The protrusion 202 may be configured to have a circular cross-sectional profile. However, the protrusion 202 may have other cross-sections and configurations which are not limited to elliptical, oblate, polygonal, irregular, or the like.

A proximal end of the stopping member 201 may be further connected or otherwise operatively coupled to a support 204 disposed around the actuating member 22. The support 204 may be configured to support the proximal end of the stopping member 201 and fix a proximal position of stopping member 201 relative to, e.g., a distal end portion of legs 16. Thus, forces applied to the distal end of legs 16 via actuating member 22 may be limited by compression of stopping member 201 against support 204, and not by the amount of force applied to actuating member 22 by, e.g., a handle coupled to actuating member 22. In some embodiments, when a force applied to the handle exceeds a predetermined limit, stopping member 201 may absorb the excess force to prevent the excess force from being transferred to the distal ends of legs 16. The protrusion 202 and/or support 204 may be formed from a resilient, flexible, conductive, and/or biocompatible material. Examples of such materials may include but are not limited to nitinol, silicone, stainless steel, metals, alloys, or the like.

The support 204 may be circular in shape. However, the support 204 may have other shapes such as a circular ring, an elliptical ring, polygonal, oblate, irregular, or the like.

A proximal end of the support 204 may further be connected or otherwise coupled to an elongated member such as a spacer 206 disposed around the actuating member 22. The spacer 206 may be configured to extend substantially from a proximal portion to a distal portion of the legs 16. The spacer 206 may be configured to provide support for preventing over-expansion of the basket 14.

The spacer 206 may be cylindrical in shape and have a cross-section of circular profile. However, the cross-section of the spacer 206 may depend on that of the actuating member 22 as, in some embodiments, the spacer 206 encompasses, or otherwise surrounds actuating member 22. The spacer 206 may also be shaped to externally support the position of the legs 16.

The spacer 206 may be formed from a resilient, flexible, and/or biocompatible material. Examples of such materials may include, but are not limited to nitinol, silicone, stainless steel, polymer, alloys, or the like.

As shown in FIG. 2, the stopping member 201 is uncompressed and the basket 14 (referring to FIG. 1) is in a first, compressed position.

Figure 3:
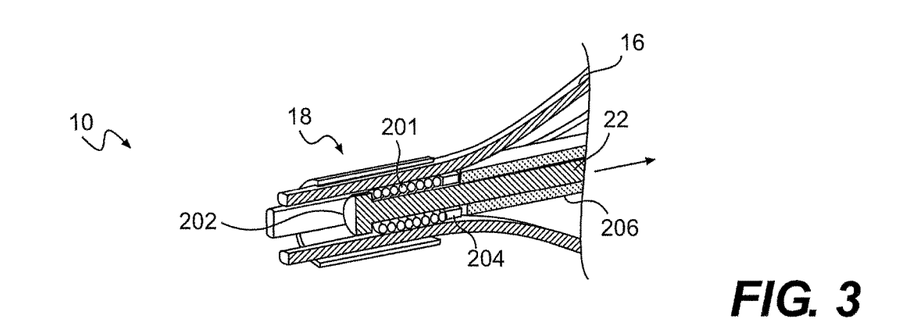
FIG. 3 is a cross-sectional side view of the medical device of FIG. 1 depicting the stopping member in a compressed position.

FIG. 3 is a cross-sectional view of the medical device 10 including the stopping member 201 in a compressed position. As the handle at the proximal end of the medical device 10 is pulled or otherwise activated to apply a proximal pulling force to actuating member 22, the protrusion 202 and the actuating member 22 may move towards the proximal end of the medical device 10. As a result, the protrusion 202 may push and compress the stopping member 201 against support 204. Due to proximal movement of the actuating member 22, the basket 14 may expand radially outward (e.g., the proximal and distal ends (not shown) of the basket 14 may move from the first position to the second position). In some embodiments, the distal ends of legs 16 may be coupled to protrusion 202 and move proximally as protrusion 202 moves proximally. In the first position, the basket 14 may be compressed (e.g., the basket 14 may appear to be closed and the legs 16 may appear to be running generally straight from the proximal end of the medical device 10 to the distal end of the distal cap 18). While in the second position, the basket 14 may be expanded such that the legs 16 are bowed radially and outwardly. Without stopping member 201, protrusion 202, and support 204, it may be possible to apply too much force to actuating member 22, e.g., by pulling or otherwise activating the handle of the medical device 10, resulting in damage to legs 16 and/or an airway wall caused by, e.g., over-expansion of basket 14. However, because the protrusion 202 may compress the stopping member 201 by only a fixed amount limited by the support 204, legs 16 may be prevented from moving beyond a predetermined limit. This may help avoid over-expansion of the basket 14 and undue flexing of legs 16. Further, due to a fixed length of the spacer 206, the legs 16 may be able to bow in a controlled manner. Hence, over-expansion of the basket 14 may be further avoided, and possible damage to the legs 16 and the airways can also be further avoided.

Further, as the handle of the medical device 10 is released, the protrusion 202 and the actuating member 22 may move towards the distal end of the distal cap 18. This distal movement may uncompress the stopping member 201, causing the legs 16 to move from the second position to the first position. That is, the release of the handle may release the force compressing stopping member 201, causing stopping member 201 to release any stored potential energy and return to an uncompressed position so that basket 14 is returned to the compressed position. Thus, as actuating member 22 may be configured to move reciprocally, legs 16 may reciprocate between the compressed, first position to the second, expanded position (e.g., as the actuating member 22 moves proximally, the legs 16 may move from the first position to the second position, and as the actuating member 22 moves distally, the legs 16 may move from the second position to the first position). It should be noted however, that alternative embodiments are also contemplated. In one alternative embodiment, the distal movement of actuating member 22 may move legs 16 from the first, compressed position to the second, expanded position, while the proximal movement of actuating member 22 moves legs 16 from the second, expanded position to the first, compressed position.

Figure 4:
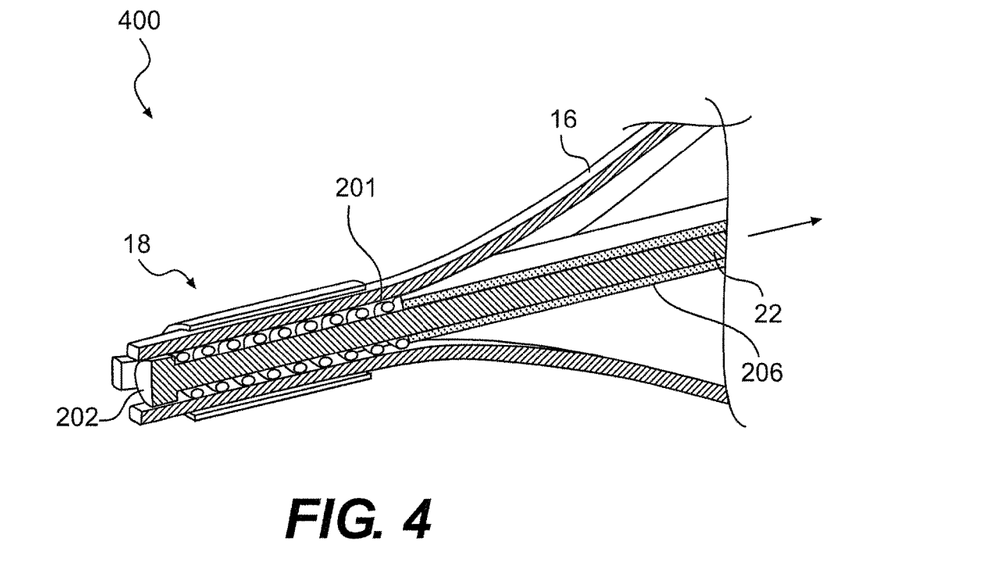
FIG. 4 is a cross-sectional side view of the medical device of FIG. 1, according to an embodiment of the present disclosure.

FIG. 4 is a cross-sectional view of the medical device 10 depicting the spacer 206 supporting the stopping member 201. In the embodiment of FIG. 4, the stopping member 201 may be directly supported by the spacer 206. Spacer 206 may be located adjacent to the proximal end of the stopping member 201, and directly fix a proximal position of stopping member 201. Thus, forces applied to the distal end of legs 16 via actuating member 22 may be limited by compression of stopping member 201 against spacer 206 and/or the stiffness of stopping member 201, and not by the amount of force applied to actuating member 22 by, e.g., a handle coupled to actuating member 22. In some embodiments, when a force applied to the handle exceeds a limit, stopping member 201 may absorb the excess force to prevent the excess force from being transferred to the distal ends of legs 16. The resiliency of the stopping member 201 can also be set such that upon actuation it provides a tactile signal to the practitioner indicating that the basket 14 is fully expanded.

Figure 5:
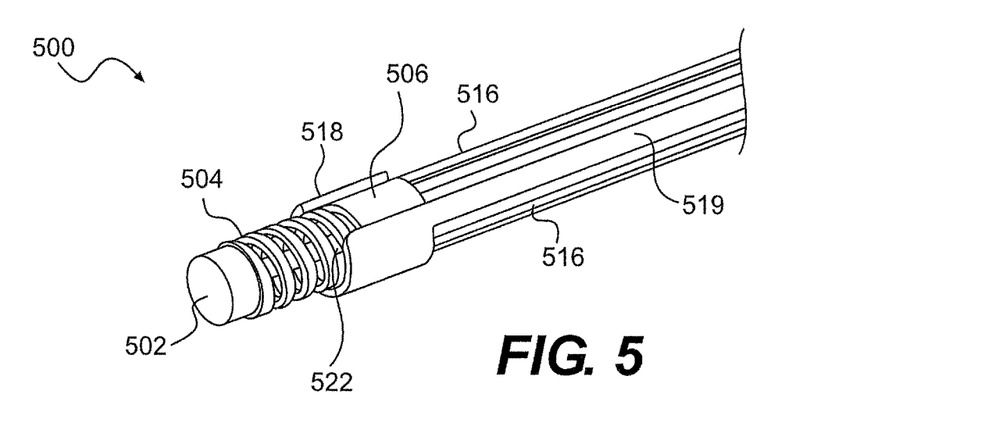
FIG. 5 is a partial perspective view of a medical device, according to an embodiment of the present disclosure.

FIG. 5 illustrates another embodiment of an exemplary medical device 500. Medical device 500 may be substantially similar to medical device 10 (referring to FIG. 1), but additionally or alternatively include a stopping member 504 integral with the distal ends of the plurality of legs 516. Legs 516 may be substantially similar to and include any one or more of the features of legs 16 described above. In an alternative embodiment, the stopping member 504 may be integral with a proximal end (not shown) of each of the plurality of the legs 516. Each of the legs 516 may include an electrode disposed along a longitudinal axis. Legs 516 may be integral and cut out from a tube having an outer diameter less than the inner diameter of a scope working channel. Alternatively, legs 516 may be cut out from a sheet of material and rolled, or may be formed by another suitable mechanism. A cap (not shown) may extend over the distal assembly. The cap may prevent tissue from entering the spaces within and limiting the compression of stopping member 504.

An actuating member 522 may extend from a proximal end (not shown) to a distal end of the medical device 500. A protrusion 502 may be disposed at a distal end of the actuating member 522. Actuating member 522 and protrusion 502 may be substantially similar to that of actuating member 22 and protrusion 202, respectively, shown in FIG. 2. Stopping member 504 may be a coiled spring or other suitable resilient member that surrounds a substantial distal portion of the actuating member 522 and may be located proximally adjacent to the protrusion 502. Stopping member 504 may be integrally connected to the distal end of each leg 516 via a support 506. That is, support 506 may be disposed between stopping member 504 and legs 516 (e.g., support 506 may be proximal to stopping member 504 and distal to the distal ends of legs 516). Support 506 may be generally cylindrical or may have any other suitable shape. In an alternative embodiment, each individual leg 516 may include a stopping member incorporated into a distal end portion (e.g., a basket having four legs 516 may include four stopping members, at least one incorporated into an end portion of each leg 516).

As actuating member 522 is pulled proximally, legs 516 may expand radially outward from a first, compressed position to a second, expanded position. Support 506 may be located adjacent to the proximal end of the stopping member 504, and directly fix a proximal position of stopping member 504. Thus, forces applied to the distal end of legs 516 via actuating member 522 may be limited by compression of stopping member 504 against support 506, and not by the amount of force applied to actuating member 22 by, e.g., a handle coupled to actuating member 22. In some embodiments, when a force applied to the handle exceeds a predetermined limit, stopping member 504 may absorb the excess force to prevent the excess force from being transferred to the distal ends of legs 516. Thus, when a basket formed by legs 516 reaches the predetermined expansion limit, further force applied to the actuation member 22 may not further expand the basket.

A distal end of a cap 518 may be configured to support stopping member 504 and the distal ends of legs 516. Cap 518 may be connected, or otherwise coupled to a distal end of an elongate member, such as, e.g., elongate member 12 (referring to FIG. 1) by an elongate connector 519. Cap 518 may be generally U-shaped, C-shaped, or have another suitable configuration.

Figure 6:
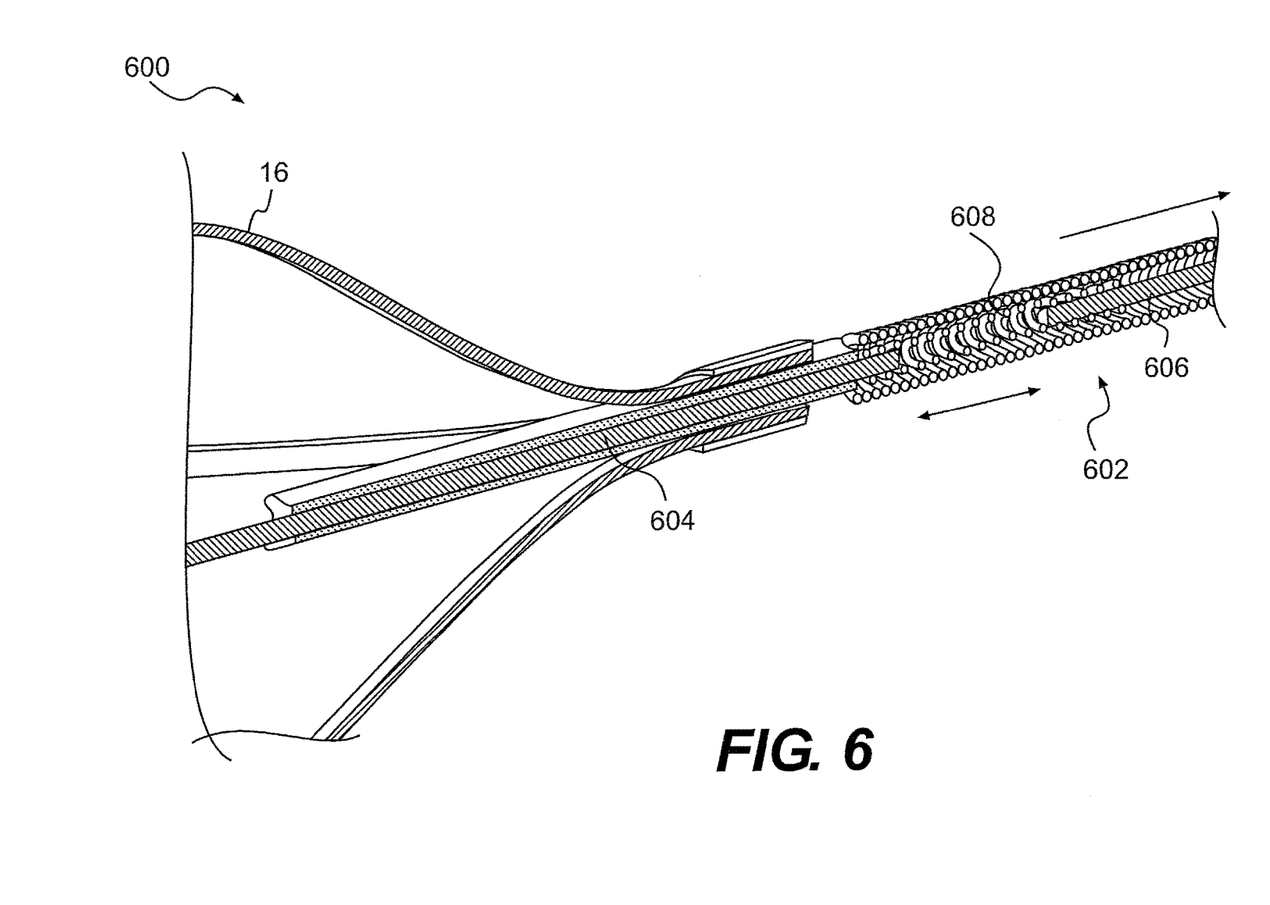
FIG. 6 is a cross-sectional view of a medical device, according to an embodiment of the present disclosure.

FIG. 6 illustrates another embodiment of a medical device 600. Medical device 600 may include a stopping member 608 disposed proximally of legs 16, and between a distal portion 604 and a proximal portion 606 of an actuating member 602. In other words, a distal end of the stopping member 608 may be connected to a proximal end of distal portion 604 of the actuating member 602 and a proximal end of the stopping member 608 may be connected to a distal end of the proximal portion 606 of the actuating member 602. Actuating member 602 may be any suitable actuating member such as a pull wire, braided pull wire, a plurality of pull wires, a control rod, or the like. In one embodiment, as actuating member 602 is moved proximally, stopping member 608 may expand, causing the legs 16 to expand to the second, expanded position. The stiffness of stopping member 608 may be selected to prevent over-expansion of actuating member 602 in the proximal direction. When a proximal force applied to actuating member 602 is below a predetermined limit, the proximal force may be insufficient to expand stopping member 608 such that distal portion 604, stopping member 608, and proximal portion 606 may all move distally while their configurations remain generally constant relative to each other. However, as the proximal force is increased, e.g., to a point that would otherwise cause over-expansion of basket 14 and legs 16 (referring to FIG. 1), stopping member 608 may expand. The expansion of stopping member 608 may absorb the excess force, preventing the excess force from causing the over-expansion of basket 14 and legs 16. As the actuating member 602 is released in the distal direction, stopping member 608 may compress, release stored energy, and thereby move the legs 516 to the first, compressed position.

A method of delivering energy to an airway treating a lung using the disclosed medical device may include a number of consecutive, non-consecutive, simultaneous, non-simultaneous, or alternative steps. At the outset, a medical device made in accordance with principles of the disclosed subject matter can be provided. An elongated device such as a bronchoscope may be inserted through a natural or surgical opening such as a mouth of the patient. The bronchoscope may be required to traverse through narrow vessels such as a wind pipe followed by bronchioles of a lung of a patient. Thereafter, a bronchiole that is targeted for treatment may be viewed and examined through the bronchoscope. This may be followed by inserting a distal portion of the medical device 10 into a lumen of the bronchoscope to reach an area of the treatment site. A handle (not shown) at a proximal end of the medical device 10 may be connected to a plug (not shown) which may further be connected to an energy generator such as an electrosurgical generator (not shown). As the handle, or other actuator, is pulled or otherwise actuated (e.g., moved proximally), protrusion 202 coupled to actuating member 22 may move toward a proximal portion of the medical device 10. The proximal movement of actuating member 22 may cause legs 16 to bow radially and outwardly enabling the electrodes disposed on the legs 16 to contact an airway wall. Meanwhile, the electrosurgical generator may be activated and an electric current may travel through the plug toward actuating member 22. Further, as actuating member 22 moves back and forth (i.e., reciprocates), the electric current may transfer from actuating member 22 to protrusion 202. Because of the contact and conductive material of the protrusion 202 and the legs 16, the electric current may be transferred to each of the legs 16 via protrusion 202. As the legs 16 bow outwardly against a wall and become electrically activated, the electrical energy may be transferred from the legs 16 to an airway wall in a controlled manner.

Embodiments of the present disclosure may be used in any medical or non-medical environment or in any other application other than in an airway, where energy is applied to a wall through a device where control of expansion legs against the wall is desired. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A medical device, comprising:
a shaft having a shaft lumen extending at least partially between a proximal end and a distal end of the shaft;
a plurality of legs proximate a distal portion of the shaft;
a distal end piece coupled to each of the plurality of legs and located distally to the distal end of the shaft;
an actuating member coupled to the distal end piece and extending between the plurality of legs and through the shaft lumen, wherein reciprocal movement of the actuating member is configured to reversibly move the plurality of legs from a first position to a second position; and
a stopping member coupled to the actuating member and at least a portion of the stopping member is disposed within the distal end piece, the stopping member defines a stopping member lumen configured to receive a portion of the actuating member, wherein proximal movement of the actuating member compresses the stopping member, and compression of the stopping member limits the proximal movement of the actuating member and radial expansion of the plurality of legs.

2. The medical device of claim 1, wherein the actuating member further includes a protrusion disposed at a distal end of the actuating member, the protrusion configured to compress the stopping member.

3. The medical device of claim 2, wherein the protrusion is a disc attached to the distal end of the actuating member, wherein the disc has a width greater than a width of the stopping member lumen.

4. The medical device of claim 3, wherein the disc engages a distal end of the stopping member to limit the movement of the actuating member.

5. The medical device of claim 4, wherein the protrusion is movable relative to distalmost ends of each of the plurality of legs.

6. The medical device of claim 5, wherein the stopping member is a spring and is:
in a first, longitudinally expanded configuration when the plurality of legs are in the first position, wherein the plurality of legs are radially compressed in the first position; and
in a second, longitudinally compressed configuration when the plurality of legs are in the second position, wherein the plurality of legs are radially expanded in the second position.

7. The medical device of claim 1, wherein the stopping member is configured to limit a movement of the actuating member along a longitudinal axis of the shaft.

8. The medical device of claim 1, further including a support disposed around the actuating member and connected to the stopping member, the support being configured to support a proximal end of the stopping member.

9. The medical device of claim 1, wherein the stopping member is formed in at least one end of each of the plurality of legs.

10. The medical device of claim 1, wherein the plurality of legs are compressed in the first position, and are configured to bow outwardly from a longitudinal axis in the second position.

11. The medical device of claim 1, wherein the stopping member is:
in a first, longitudinally expanded configuration when the plurality of legs are in the first position, wherein the plurality of legs are radially compressed in the first position; and
in a second, longitudinally compressed configuration when the plurality of legs are in the second position, wherein the plurality of legs are radially expanded in the second position.

12. A medical device, comprising:
a shaft having a lumen extending at least partially between a proximal end and a distal end of the shaft;
a plurality of legs proximate a distal portion of the shaft;
a distal end piece coupled to each of the plurality of legs and located distally to the distal end of the shaft;
an actuating member coupled to the distal end piece and extending between the plurality of legs and through the lumen, wherein reciprocal movement of the actuating member is configured to reversibly move the plurality of legs from a first, radially-collapsed, position to a second, radially expanded, position; wherein the actuating member includes a first portion having a proximal end and a distal end, and a second portion having a proximal end and a distal end, the proximal end of the second portion being distal to the distal end of the first portion; and a stopping member coupled to the actuating member and configured to limit a movement of the actuating member, wherein the stopping member is disposed proximal to the plurality of legs and the stopping member also is disposed between the distal end of the first portion and the proximal end of the second portion, and:

when the plurality of legs are in the first position, application of a proximal force to the actuating member below a threshold amount moves the plurality of legs toward the second position; and after the plurality of legs have been moved from the first position toward the second position, application of a proximal force to the actuating member above the threshold amount expands the stopping member to prevent further radial expansion of the plurality of legs.

13. The medical device of claim 12, wherein application of a proximal force below the threshold amount is insufficient to expand the stopping member.

14. The medical device of claim 13, wherein, after the stopping member has expanded, release of the proximal force enables the stopping member to compress, the actuating member to move distally, and the plurality of legs to move back to the first position.

15. The medical device of claim 14, wherein the stopping member is a spring.

16. A medical device, comprising:
a shaft having a lumen extending between a proximal end and a distal end of the shaft;
a plurality of legs extending from the distal end of the shaft, wherein:
   at least one of the legs includes an electrode for delivering energy; and
   wherein each of the plurality of legs includes a distal end;
a distal end piece coupled to the distal end of each of the plurality of legs;
an actuating member coupled to the distal end piece and extending between the plurality of legs and through the lumen, the actuating member configured to reversibly move the plurality of legs from a first position to a second position, wherein:
the plurality of legs move from the first position to the second position when a proximal force is applied to the actuating member; and
the plurality of legs move from the second position to the first position when the proximal force is released; and
a stopping member coupled to the actuating member and at least a portion of the stopping member is disposed within the distal end piece, the stopping member defines a stopping member lumen configured to receive a portion of the actuating member, wherein compression of the stopping member limits radial expansion of the plurality of legs.

* * * * *